United States Patent [19]

Phillips et al.

[11] Patent Number: 5,696,293

[45] Date of Patent: Dec. 9, 1997

US005696293A

[54] CATALYST COMPOSITION FOR PRODUCING POLYETHER POLYAMINE AND PRODUCTION METHOD OF POLYETHER POLYAMINE BY USE OF THE CATALYSTS COMPOSITION

[75] Inventors: Christopher Harold Phillips, W. Yorks, United Kingdom; Yoji Hirasawa, Soraku; Keiichi Okajima, Katano, both of Japan; Julius John Batty, Winsford; Brian Lewis Booth, Stockport, both of United Kingdom

[73] Assignee: Nippon Paint Co., Ltd., Osaka, Japan

[21] Appl. No.: 625,933

[22] Filed: Apr. 1, 1996

Related U.S. Application Data

[62] Division of Ser. No. 203,361, Mar. 1, 1994, abandoned.

[30] Foreign Application Priority Data

Mar. 1, 1993 [JP] Japan ................... 039822/1993
Feb. 23, 1994 [GB] United Kingdom ............... 9403467

[51] Int. Cl.[6] ................... C07C 209/16; C07C 209/26
[52] U.S. Cl. ................... 564/480; 564/479; 564/478; 564/472; 564/469; 564/474; 502/332
[58] Field of Search ................... 564/474, 192, 564/197, 198, 199, 215, 224, 399, 402, 480, 472, 478, 479

[56] References Cited

U.S. PATENT DOCUMENTS

| | | | |
|---|---|---|---|
| 4,847,231 | 7/1989 | Gratzel et al. | 502/326 |
| 4,952,549 | 8/1990 | Immel et al. | 502/330 |
| 5,015,773 | 5/1991 | Dobson | 564/474 |
| 5,093,528 | 3/1992 | Dobson et al. | 564/472 |
| 5,208,207 | 5/1993 | Stonehart et al. | 502/339 |
| 5,356,851 | 10/1994 | Sarrazin et al. | 502/332 |

FOREIGN PATENT DOCUMENTS

| | | | |
|---|---|---|---|
| 5092289 | 7/1975 | Japan | 502/333 |
| 0333963 | 3/1972 | U.S.S.R. | 502/333 |

*Primary Examiner*—Glenn A. Caldarola
*Assistant Examiner*—Bekir L. Yildirim
*Attorney, Agent, or Firm*—Wenderoth, Lind & Ponack

[57] ABSTRACT

The present invention provides a catalyst composition for producing a polyether polyamine, comprising:
(a) ruthenium and
(b) at least one of metals selected from the group consisting of palladium, platinum, rhodium, osmium, iridium, rhenium, technetium, molybdenum and tungsten on a carrier.

7 Claims, No Drawings

CATALYST COMPOSITION FOR PRODUCING POLYETHER POLYAMINE AND PRODUCTION METHOD OF POLYETHER POLYAMINE BY USE OF THE CATALYSTS COMPOSITION

This application is a division of now abandoned Ser. No. 08/203,361 filed Mar. 1, 1994 now abandoned.

BACKGROUND OF THE INVENTION

1. Field of the Invention

The present invention relates to a catalyst composition for producing polyether polyamine, which is useful for a hardening agent for paint or molding compound.

2. Description of the Prior Art

Polyether polyamine has been widely used as a hardening agent or a raw material for polyamide. A known useful production method of polyether polyamine is that polyether polyol is treated directly with ammonia and hydrogen in the presence of a catalyst. Such an amination reaction of polyether polyol may undergo the following reaction mechanisms: (1) a hydroxy group is dehydrogenated to form a ketone group, (2) ammonia is added to the ketone group to form an aminol group, (3) the aminol group is dehydrated to form an imino group and (4) hydrogen is added to the imino group to form an amino group. All the steps of the above (1) to (4) are needed to proceed smoothly in order to give polyether polyamine at a high efficiency. In such a reaction, nickel is usually used as a catalyst for surface catalyzed reduction. Therefore nickel may be an essential metal in a catalyst for producing polyether polyamine.

For example, British patent No. 2,175,910 discloses that molybdenum is added to improve activity of Raney nickel catalyst. The Raney nickel catalyst, however, does not display sufficient activity. It takes a long reaction time (LHSV=0.1–2.0; LHSV means hourly space velocity of liquid; reaction time becomes shorter as the value becomes larger) and needs a high pressure (more than 13 MPa in a continuous system) to directly change polyether polyol to amine in the presence of the above Raney nickel. Therefore it is difficult to manufacture it on a technical scale.

European patent application No. 0356,047A2 discloses a catalyst for surface catalyzed reduction in which nickel, ruthenium and other transition metals are loaded on a γ-alumina support. However, this catalyst also does not display sufficient activity, so that a manufacturing practice on a technical scale is almost impossible.

Moreover the catalysts above mentioned are sensitive to a catalyst poison, such as water. For example, when water is contained at an amount of about 5% to polyol as a raw material in a reaction system, the conversion is lowered about 50%. A catalyst based on nickel which is excellent enough to be applied to a technical manufacturing method in which the reaction may be carried out in a short time and at a low pressure has not been prepared yet.

SUMMARY OF THE INVENTION

The object of the present invention is to provide a catalyst composition for producing polyether polyamine with high conversion in a batch or continuous system even under such reaction conditions that a molar ratio of hydrogen and ammonia to a hydroxy group is relatively low, the catalyst composition having a high activity at a low pressure even under high LHSV conditions and being hardly influenced by catalyst poison such as water.

Another object of the present invention is to provide a method for producing polyether polyamine with high conversion and selectivity by use of the above catalyst composition.

DETAILED DESCRIPTION OF THE INVENTION

The present invention provides a catalyst composition for producing polyether polyamine with high conversion even under such reaction conditions that a molar ratio of hydrogen and ammonia to a hydroxy group is relatively low, the catalyst composition having a high activity at a low pressure even under high LHSV conditions and being hardly influenced by catalyst poison such as water.

The present invention also provides a method for producing polyether polyamine with high conversion and selectivity by use of the above catalyst composition. The present invention has accomplished the above object by a catalyst composition containing ruthenium in combination with a specified transition metal.

When nickel, which has been thought to be essential to a catalyst for producing polyether polyamine, is combined with ruthenium, the activity is deteriorated.

In more detail, the present invention relates to a catalyst composition for producing polyether polyamine, comprising:

(a) ruthenium and
(b) at least one of metals selected from the group consisting of palladium, platinum, rhodium, osmium, iridium, rhenium, technetium, molybdenum and tungsten on a support.

The support for the catalyst is not particularly limited in so far as it is one used usually as a support for surface-catalyzed reduction. Preferable support is selected from the group consisting of γ-alumina, carbon, silica-alumina, silica-titanium oxide and diatomaceous earth. Alpha-γ-alumina, silica and titanium dioxide may be used as a support.

Ruthenium is indispensable as a metal loaded on the support (hereinafter referred to as "catalytic metal"). Ruthenium works highly effectively in dehydrogenation reaction and hydrogenation reaction.

At least one metal selected preferably from the group consisting of atoms in periodic raws 5 to 6 of groups VIA, VIIA and VIII of the periodic table may be used as a catalytic metal loaded on a support in combination with ruthenium. In more detail, it is preferable to use palladium, platinum, rhodium, osmium, iridium, rhenium, technetium, molybdenum, or tungsten as a catalytic metal. More preferably, one of the metals selected from the group consisting of palladium, platinum, rhodium, osmium, and rhenium is used. Such a catalytic metal promotes the activity of ruthenium and prevents inactivation of ruthenium by a catalyst poison. The most preferable metal loaded on a support in combination with ruthenium is palladium.

Ruthenium is contained at an amount of 0.1–30% by weight, preferably 0.5–10% by weight, more preferably 0.5–5% by weight on the basis of the total weight of the catalyst composition. If the content is less than 0.1% by weight, the activity of the catalyst composition is insufficient. If the content is more than 30% by weight, ruthenium does not enhance the conversion any more.

The metal loaded on a support in combination with ruthenium is contained at an amount of 0.1–30% by weight, preferably 0.5–10% by weight, more preferably 0.5–5% by weight on the basis of a total weight of the catalyst composition. If the content is less than 0.1% by weight, the activity of the catalyst composition is insufficient. If the content is more than 30% by weight, the loaded metal highly cover the supported surface and prevents its catalytic activity.

Ruthenium and the above-mentioned catalytic metal are loaded on a support in a total amount of 0.2 to 60% by weight, preferably 1-20% by weight, more preferably 1-10% by weight on the basis of a total weight of the catalyst composition. A catalyst composition including ruthenium and the supported metal in an amount outside the range cannot function effectively, because when the amount of ruthenium and the supported metal is below 0.2% by weight, the activity of the catalyst composition is insufficient, and when the amount is more than 60% by weight, the function of the carrier is inhibited by the metals covering the carrier. It is preferable that at least ruthenium and palladium are loaded on a support as supported metals, and it is more preferable that ruthenium is loaded on a support in an amount of 0.5% by weight or more.

Methods that are normally used in the art can be used for loading a catalytic metal on a support. Such methods include a precipitating method, impregnating method, ion exchanging method and the like.

The catalyst composition of the present invention can be prepared in a desired size and shape by a standard method such as a crush, after catalytic metals are loaded on a support. The size and shape of the catalyst composition is not limited but a catalyst composition with the shape of a sphere or a pellet with the size of 2 to 3 mm is preferable.

The present invention also relates to a method for producing polyether polyamine, including a process characterized in that polyether polyol is brought into contact with the above-mentioned catalyst composition together with hydrogen and ammonia.

Polyether polyol used as a raw material in the present invention is used in a variety of arts and is not limited. Preferable ones are those obtained by a ring-opening polymerization of alkylene oxides, such as ethylene oxide, propylene oxide, butylene oxide and tetrahydrofuran. The molecular weight of polyether polyol is not limited but 20000 or less is preferable. When polyether polyol having a molecular weight of more than 20000 is used, a high conversion cannot be accomplished, because a molar ratio of hydrogen and ammonia to a single polyether polyol molecule becomes low, and therefore, a reaction between polyether polyol and hydrogen and ammonia is determined by a diffusion. For a continuous reaction, polyether polyol is preferably liquid at a room temperature. Polyether polyol having 2 to 8 functional groups is preferably used. Polyether polyol having one functional group can be synthesized, but it is not useful for an industrial purpose. Polyether polyol having more than 8 functional groups is not preferable, because it readily solidifies.

In a reaction between polyether polyol, hydrogen and ammonia, a molar ratio of OH (in polyether polyol)/$NH_3$/$H_2$ is preferably 1/10-40/0.5-10, and more preferably, it is 1/15-30/1-5. When a molar ratio of hydrogen to a hydroxy group is less than 0.5, a hydrogenation reaction cannot proceed smoothly and conversion and selectivity are lowered. When a molar ratio of hydrogen to a hydroxy group is more than 10, conversion and selectivity cannot increase in proportion to the addition of hydrogen but rather decrease, and the amination reaction cannot be carried out at a low pressure. When a molar ratio of ammonia to a hydroxy group is less than 10, conversion and selectivity are lowered, although the reasons for the low conversion and selectivity are unclear. When a molar ratio of ammonia to a hydroxy group is more than 40, conversion and selectivity cannot increase and the amination reaction cannot be carried out at a low pressure. The term "a low pressure" as used herein means a pressure up to 20 MPa for a batch reaction and 10 MPa for a continuous reaction.

Amination reactions can be done by standard methods including a batch system and a continuous system. The reactions are preferably done at a pressure within the range of 10 to 20 MPa for a batch reaction and 4 to 10 MPa and more preferably, 5 to 10 MPa for a continuous reaction. When a reaction pressure is less than the above-mentioned level, conversion and selectivity are lowered. When a pressure is more than the above-mentioned level, conversion and selectivity cannot increase and a reaction at such pressure is no longer a low pressure reaction, which is one of the features of the present invention. The reactions are preferably done at temperatures of 170° to 250° C. and more preferably 200° to 220° C. The reactions done at a temperature outside of the above-mentioned level are not preferable, because when a reaction temperature is less than 170° C., conversion is lowered and when a reaction temperature is more than 250° C., polyol is decomposed and catalyst is deteriorated. The reactions are done at LHSV of 10 or less and preferably within a range of 2 to 10. When LHSV is more than 10, conversion and selectivity are lowered.

An amount of the catalyst composition of the present invention used in the amination reaction depends on a composition of the catalyst, a polyol, which is to be converted to amine, and a reaction system. However generally in a batch system the amount shall be 1-50% of a reactant polyol. If the amount of the catalyst composition is too small, the conversion and selectivity are lowered. If the catalyst composition is too large, it does not enhance the conversion and selectivity.

EXAMPLES

The present invention is further illustrated by the following examples. Of course, the scope of the present invention shall not be limited to the following examples.

A. Batch Reaction System

1) Preparation and Activation of Catalyst

A predetermined amount of a catalyst (5.0 g unless otherwise described in the following Examples) was put in a reaction vessel with a capacity of 500 ml. After the air in the vessel was replaced by nitrogen, the catalyst was activated at a temperature of 200° C. or more, reduced in the presence of hydrogen for two hours, and cooled to a room temperature.

2) Charge of Polyol

Then, 100 g of a polypropylene glycol with a molecular weight of 2000 was put in a cylinder with a capacity of 150 ml, which was connected to the reaction vessel through a bulb. After air in the cylinder was removed, a pressure was applied to about 10 atmospheric pressures by nitrogen, and then the polypropylene glycol was added to the vessel through the valve.

3) Charge of Ammonia and Hydrogen

A predetermined amount of ammonia was charged in a cylinder with a capacity of 150 ml, which was connected to the reaction vessel through a valve. Ammonia was charged to the vessel after the cylinder was heated to about 70° C. In a similar manner, hydrogen was charged to the vessel from a hydrogen cylinder connected to the vessel through a valve until a predetermined pressure was given.

In the above process, ammonia and hydrogen were charged so that a molar ratio of OH/$NH_3$/$H_2$ in the reaction vessel would be 1/30/5. After all the ingredients were added, the vessel was heated to a predetermined temperature while the round speed of a stirring apparatus was maintained about 1200 rpm. After the reaction system was kept for one hour, the vessel was cooled to a room temperature and a pressure in the vessel was lowered to the atmospheric pressure. The mixture in the vessel was taken out, filtered to remove a catalyst and distilled to remove ammonia and water dissolved in the mixture, thereby polyether polyamine was given. Conversion of a hydroxy group to an amino group and selectivity were evaluated by measuring an amine value.

The terms "conversion" and "selectivity" as used in this specification are defined herein as follows.

$$\text{Conversion} = \frac{\text{moles of amine produced}}{\text{moles of OH group in polyether polyol fed of charged}} \times 100$$

$$\text{Selectivity} = \frac{\text{moles of primary amine produced}}{\text{moles of amine produced}} \times 100$$

Examples 1 to 7 and Comparative Examples 1 to 12

Conversion and selectivity (a ratio of primary amination) in the above-mentioned batch reaction systems with the use of a catalyst composition comprising ruthenium, palladium and/or other metals are shown in Table 1. The conversion and selectivity of the batch reaction systems, which were treated in a manner similar to those in Examples 1 to 7, with the use of a ruthenium alone as a catalyst or with the use of ruthenium and nickel as a catalyst are also shown in Table 1 (Comparative Examples 1 to 12). These results indicate that when palladium, molybdenum, platinum, or rhenium is added to a ruthenium-supported catalyst, the reactivity is improved and that nickel, which has been known as a metal catalyst for amination, restrains progress of reactions when nickel is added to a ruthenium-palladium catalytic system.

TABLE 1

| catalyst | | conversion (%) | selectivity (%) |
|---|---|---|---|
| Ex 1 | 2.5%Ru—2.5%Pd/γ-alumina | 97.4 | 99.8 |
| Ex 2 | 1.0%Ru—1.0%Pd/γ-alumina | 88.7 | 99.3 |
| Ex 3 | 1.5%Ru—0.5%Pd/γ-alumina | 93.1 | 99.6 |
| Ex 4 | 0.5%Ru—1.5%Pd/γ-alumina | 90.1 | 99.2 |
| Ex 5 | 1.5%Ru—0.5%Mo/γ-alumina | 87.4 | 98.9 |
| Ex 6 | 1.5%Ru—1.5%Pt/γ-alumina | 88.7 | 98.3 |
| Ex 7 | 1.5%Ru—0.5%Re/γ-alumina | 90.1 | 99.0 |
| CE 1 | 2%Ru/γ-alumina | 70.5 | 99.3 |
| CE 2 | 3.5%Ru/γ-alumina | 76.2 | 99.5 |
| CE 3 | 5%Ru/γ-alumina | 70.5 | 99.4 |
| CE 4 | 5%Ru/carbon | 72.5 | 99.6 |
| CE 5 | 2%Ru/carbon | 63.1 | 98.8 |
| CE 6 | 2.5%Ru—2.5%Pd—48%Ni/γ-alumina | 41.8 | 98.4 |
| CE 7 | 2.5%Ru—2.5%Pd—37%Ni/γ-alumina | 54.7 | 99.1 |
| CE 8 | 2%Ru—20%Ni/γ-alumina | 33.2 | 98.9 |
| CE 9 | 1%Ru—37%Ni/γ-alumina | 67.1 | 99.4 |
| CE 10 | 2%Ru—37%Ni/γ-alumina | 56.4 | 99.3 |
| CE 11 | 3.5%Ru—37%Ni/γ-alumina | 64.0 | 91.0 |
| CE 12 | 5%Ru—37%Ni/γ-alumina | 68.9 | 99.7 |

EX: Example
CE: Comparative Example

Examples 8 and Comparative Examples 13 to 16

Reactions were done in a manner similar to Example 1, except that 5 g of water was added to the reaction vessel. The results are shown in Table 2. Reactions with the use of a Raney nickel- or ruthenium-supported catalyst were also done and the influences of the water on the reactions were evaluated. These results are also shown in Table 2. These results indicate that conversion With the use of the catalyst composition of the present invention is not lowered much in the presence of water.

TABLE 2

| | catalyst | amount of water | conversion (%) | selectivity (%) |
|---|---|---|---|---|
| Ex 8 | 2.5%Ru—2.5%Pd/γ-alumina | 5.0 | 88.7 | 99.8 |
| Ex 1 | 2.5%Ru—2.5%Pd/γ-alumina | — | 97.4 | 99.8 |
| CE 13 | Raney-Ni(7.2 g) | 5.0 | 33.3 | 98.5 |
| CE 14 | Raney-Ni(7.2 g) | — | 65.3 | 99.2 |
| CE 15 | 2%Ru/carbon | 5.0 | 24.8 | 97.9 |
| CE 5 | 2%Ru/carbon | — | 63.1 | 98.8 |
| CE 16 | 2%Ru/γ-alumina | 5.0 | 64.3 | 99.4 |
| CE 1 | 2%Ru/γ-alumina | — | 70.5 | 99.3 |

EX: Example
CE: Comparative Example

B. Method for Continuous Reaction System

A catalyst activated by the same procedure as described above in Batch Reaction System was placed in a continuous reaction vessel with a capacity of 250 ml, the upper and bottom parts of which were filled with Raschig ring. An amount of the catalyst was 100 ml. The vessel was heated to 150° C. for about 45 minutes in the flow of a nitrogen gas at a pressure of 2.5 MPa and a rate of 60 liter/hour (converted into a rate at an atmospheric pressure). Then the vessel was heated to 200° C. and the temperature was maintained for about 30 minutes in the flow of a hydrogen gas. Pressure was applied to the vessel until a predetermined level was accomplished in the flow of a hydrogen gas alone and then ammonia and polypropylene glycol with a molecular weight of 2000 were continuously fed to the vessel by a pump at a constant LHSV to attain a specified molar ratio of OH/NH$_3$/H$_2$. The resulting mixture was filtered to remove a catalyst and distilled to remove water and ammonia included in the mixture, thereby polyether polyamine was obtained. The analysis similar to that in a method for the above batch reaction was made.

Examples 9 to 13 and Comparative Examples 17 to 21

A ruthenium-palladium-supported catalyst was used in the above Continuous Reaction System. The results are shown in Table 3 (Examples 9 to 13). The results with the use of a ruthenium alone as a catalyst are also shown in Table 3 (Comparative Examples 17 to 21). These results indicate that even when LHSV was as high as 3 or more, a conversion efficiency with the use of the catalyst composition of the present invention is high.

TABLE 3

| | catalyst | OH/NH$_3$/H$_2$ a molar ratio | pressure (MPa) | LHSV | conversion (%) | selectivity (%) |
|---|---|---|---|---|---|---|
| EX 9 | 2.5%Ru—2.5%Pd/γ-alumina | 1:30:5.0 | 10.0 | 3 | 94.6 | 98.9 |
| Ex 10 | 2.5%Ru—2.5%Pd/γ-alumina | 1:30:5.0 | 10.0 | 4 | 82.8 | 99.5 |
| Ex 11 | 2.5%Ru—2.5%Pd/γ-alumina | 1:30:5.0 | 10.0 | 5 | 72.5 | 98.0 |
| Ex 12 | 2.5%Ru—2.5%Pd/γ-alumina | 1:30:5.0 | 10.0 | 6 | 62.0 | 98.8 |
| Ex 13 | 2.5%Ru—2.5%Pd/γ-alumina | 1:30:5.0 | 10.0 | 7 | 56.9 | 99.5 |
| CE 17 | 5%Ru/γ-alumina | 1:30:5.0 | 10.0 | 3 | 65.3 | 98.8 |
| CE 18 | 5%Ru/γ-alumina | 1:30:5.0 | 10.0 | 4 | 55.4 | 98.5 |
| CE 19 | 5%Ru/γ-alumina | 1:30:5.0 | 10.0 | 5 | 48.2 | 98.4 |
| CE 20 | 5%Ru/γ-alumina | 1:30:5.0 | 10.0 | 6 | 42.8 | 99.9 |
| CE 21 | 5%Ru/γ-alumina | 1:30:5.0 | 10.0 | 7 | 38.6 | 99.5 |

EX: Example
CE: Comparative Example

Examples 14 to 20 and Comparative Examples 22 to 28

Continuous reactions were done with the use of a ruthenium-palladium-supported catalyst at two levels of LHSV. Four levels of pressure were applied to the reactions. The results are shown in Table 4. The results with the use of a ruthenium alone as a catalyst are also shown in Table 4. These results indicate that a conversion with the use of the catalyst composition of the present invention is high, even when a reaction is done at a low pressure.

TABLE 4

| | catalyst | OH/NH$_3$/H$_2$ a molar ratio | pressure (MPa) | LHSV | conversion (%) | selectivity (%) |
|---|---|---|---|---|---|---|
| Ex 14 | 2.5%Ru—2.5%Pd/γ-alumina | 1:30:5.0 | 3 | 5 | 54.6 | 99.5 |
| Ex 15 | 2.5%Ru—2.5%Pd/γ-alumina | 1:30:5.0 | 5 | 5 | 73.0 | 98.6 |
| Ex 16 | 2.5%Ru—2.5%Pd/γ-alumina | 1:30:5.0 | 7 | 5 | 71.3 | 99.7 |
| Ex 11 | 2.5%Ru—2.5%Pd/γ-alumina | 1:30:5.0 | 10 | 5 | 72.5 | 98.0 |
| Ex 17 | 2.5%Ru—2.5%Pd/γ-alumina | 1:30:5.0 | 3 | 3.3 | 73.5 | 99.6 |
| Ex 18 | 2.5%Ru—2.5%Pd/γ-alumina | 1:30:5.0 | 5 | 3.3 | 91.5 | 98.8 |
| Ex 19 | 2.5%Ru—2.5%Pd/γ-alumina | 1:30:5.0 | 7 | 3.3 | 90.0 | 99.1 |
| Ex 20 | 2.5%Ru—2.5%Pd/γ-alumina | 1:30:5.0 | 10 | 3.3 | 91.2 | 99.2 |
| CE 22 | 5%Ru/γ-alumina | 1:30:5.0 | 4 | 5 | 39.5 | 99.5 |
| CE 23 | 5%Ru/γ-alumina | 1:30:5.0 | 5 | 5 | 42.5 | 99.2 |
| CE 24 | 5%Ru/γ-alumina | 1:30:5.0 | 7.5 | 5 | 49.6 | 98.9 |
| CE 19 | 5%Ru/γ-alumina | 1:30:5.0 | 10 | 5 | 48.2 | 98.4 |
| CE 25 | 5%Ru/γ-alumina | 1:30:5.0 | 4 | 3.3 | 50.2 | 98.5 |
| CE 26 | 5%Ru/γ-alumina | 1:30:5.0 | 5 | 3.3 | 53.8 | 98.6 |
| CE 27 | 5%Ru/γ-alumina | 1:30:5.0 | 7.5 | 3.3 | 62.1 | 99.5 |
| CE 28 | 5%Ru/γ-alumina | 1:30:5.0 | 10 | 3.3 | 62.9 | 99.1 |

EX: Example
CE: Comparative Example

Examples 21 to 35 and Comparative Examples 29 to 40

Continuous reactions were done with the use of a ruthenium-palladium-supported catalyst at two levels of LHSV. The molar ratio of hydrogen and ammonia to a hydroxy group was varied. The results are shown in Table 5. The results with the use of ruthenium alone as a catalyst (other reactions were done in a manner similar to Example 21-29) are shown in Table 5. These results indicate that a conversion with the use of the catalyst composition of the present invention is high, even when a reaction is done at a low molar ratio of hydrogen and ammonia to a hydroxy group.

TABLE 5

| catalyst | OH/NH$_3$/H$_2$ a molar ratio | pressure (MPa) | LHSV | conversion (%) | selectivity (%) |
|---|---|---|---|---|---|
| Ex 21 | 2.5%Ru—2.5%Pd/γ-alumina | 1:30:2.0 | 10 | 5 | 81.1 | 99.5 |
| Ex 22 | 2.5%Ru—2.5%Pd/γ-alumina | 1:30:2.5 | 10 | 5 | 80.4 | 99.6 |
| Ex 23 | 2.5%Ru—2.5%Pd/γ-alumina | 1:30:3.0 | 10 | 5 | 78.9 | 99.2 |
| Ex 24 | 2.5%Ru—2.5%Pd/γ-alumina | 1:30:4.0 | 10 | 5 | 77.7 | 99.3 |
| Ex 11 | 2.5%Ru—2.5%Pd/γ-alumina | 1:30:5.0 | 10 | 5 | 72.5 | 98.0 |
| Ex 25 | 2.5%Ru—2.5%Pd/γ-alumina | 1:30:2.0 | 10 | 3.3 | 99.0 | 98.9 |
| Ex 26 | 2.5%Ru—2.5%Pd/γ-alumina | 1:30:2.5 | 10 | 3.3 | 98.5 | 99.1 |
| Ex 27 | 2.5%Ru—2.5%Pd/γ-alumina | 1:30:3.0 | 10 | 3.3 | 97.8 | 99.4 |
| Ex 28 | 2.5%Ru—2.5%Pd/γ-alumina | 1:30:3.5 | 10 | 3.3 | 96.6 | 99.7 |
| Ex 29 | 2.5%Ru—2.5%Pd/γ-alumina | 1:30:4.0 | 10 | 3.3 | 96.2 | 99.5 |
| Ex 20 | 2.5%Ru—2.5%Pd/γ-alumina | 1:30:5.0 | 10 | 3.3 | 91.2 | 99.2 |
| CE 29 | 5%Ru/γ-alumina | 1:30:2.5 | 10 | 5.0 | 25.8 | 98.5 |
| CE 30 | 5%Ru/γ-alumina | 1:30:3.0 | 10 | 5.0 | 38.4 | 97.6 |
| CE 31 | 5%Ru/γ-alumina | 1:30:4.0 | 10 | 5.0 | 46.7 | 98.5 |
| CE 19 | 5%Ru/γ-alumina | 1:30:5.0 | 10 | 5.0 | 48.2 | 98.4 |
| CE 32 | 5%Ru/γ-alumina | 1:30:2.5 | 10 | 3.3 | 33.6 | 99.1 |
| CE 33 | 5%Ru/γ-alumina | 1:30:3.0 | 10 | 3.3 | 48.3 | 99.0 |
| CE 34 | 5%Ru/γ-alumina | 1:30:4.0 | 10 | 3.3 | 57.2 | 99.6 |
| CE 28 | 5%Ru/γ-alumina | 1:30:5.0 | 10 | 3.3 | 62.9 | 99.1 |
| Ex 30 | 2.5%Ru—2.5%Pd/γ-alumina | 1:15:5.0 | 10 | 5.0 | 73.1 | 99.5 |
| Ex 31 | 2.5%Ru—2.5%Pd/γ-alumina | 1:20:5.0 | 10 | 5.0 | 74.5 | 99.8 |
| Ex 32 | 2.5%Ru—2.5%Pd/γ-alumina | 1:25:5.0 | 10 | 5.0 | 73.9 | 99.5 |
| Ex 11 | 2.5%Ru—2.5%Pd/γ-alumina | 1:30:5.0 | 10 | 5.0 | 72.5 | 98.0 |
| Ex 33 | 2.5%Ru—2.5%Pd/γ-alumina | 1:15:5.0 | 10 | 3.3 | 89.2 | 99.7 |
| Ex 34 | 2.5%Ru—2.5%Pd/γ-alumina | 1:20:5.0 | 10 | 3.3 | 91.5 | 99.6 |
| Ex 35 | 2.5%Ru—2.5%Pd/γ-alumina | 1:25:5.0 | 10 | 3.3 | 92.8 | 99.5 |
| Ex 20 | 2.5%Ru—2.5%Pd/γ-alumina | 1:30:5.0 | 10 | 3.3 | 91.2 | 99.2 |
| CE 35 | 5%Ru/γ-alumina | 1:15:5.0 | 10 | 5.0 | 35.8 | 99.5 |
| CE 36 | 5%Ru/γ-alumina | 1:20:5.0 | 10 | 5.0 | 48.4 | 99.5 |
| CE 37 | 5%Ru/γ-alumina | 1:25:5.0 | 10 | 5.0 | 48.4 | 99.1 |
| CE 19 | 5%Ru/γ-alumina | 1:30:5.0 | 10 | 5.0 | 48.2 | 98.4 |
| CE 38 | 5%Ru/γ-alumina | 1:15:5.0 | 10 | 3.3 | 38.6 | 99.1 |
| CE 39 | 5%Ru/γ-alumina | 1:20:5.0 | 10 | 3.3 | 58.3 | 99.0 |
| CE 40 | 5%Ru/γ-alumina | 1:25:5.0 | 10 | 3.3 | 60.2 | 99.6 |
| CE 28 | 5%Ru/γ-alumina | 1:30:5.0 | 10 | 3.3 | 62.9 | 99.1 |

EX: Example
CE: Comparative Example

Examples 36 and 37

Reactions were done in a manner similar to Example 7 by use of a ruthenium-palladium-platinum-supported catalyst. The results are shown in Table 6.

TABLE 6

| catalyst | conversion (%) | selectivity (%) |
|---|---|---|
| Ex 36 | 3.75%Ru—1.25%Pd—0.1%Pt/γ-alumina | 99.0 | 99.7 |
| Ex 37 | 2.5%Ru—2.5%Pd—0.1%Pt/γ-alumina | 98.5 | 99.8 |
| CE 6 | 2.5%Ru—2.5%Pd—48%Ni/γ-alumina | 41.8 | 98.4 |
| CE 7 | 2.5%Ru—2.5%Pd—37%Ni/γ-alumina | 54.7 | 99.1 |

EX: Example
CE: Comparative Example

Example 38

Reaction was done in a manner similar to Example 1 by use of a carbon support instead of an alumina support. The results are shown in Table 7.

TABLE 7

| catalyst | conversion (%) | selectivity (%) |
|---|---|---|
| Ex 38 | 2.5%Ru—2.5%Pd/carbon | 87.5 | 99.8 |
| EX 1 | 2.5%Ru—2.5%Pd/γ-alumina | 97.4 | 99.8 |

EX: Example
CE: Comparative Example

What is claimed is:

1. A method of producing a polyether polyamine comprising contacting a polyether polyol with hydrogen and ammonia in the presence of a catalyst composition consisting essentially of (a) ruthenium and (b) at least one metal selected from the group consisting of palladium, platinum, rhodium, osmium, iridium, rhenium, technetium, molybdenum and tungsten on a support.

2. The method of claim 1, in which the method is allowed to continuously proceed.

3. The method of claim 1, in which the catalyst composition contains the ruthenium in an amount of 0.1–30% by weight on the basis of the total weight of the catalyst composition.

4. The method of claim 1, in which the catalyst composition contains said at least one metal in an amount of 0.1–30% by weight on the basis of the total weight of the catalyst composition.

5. The method of claim 1, in which the total amount of (a) and (b) is 0.2–60% by weight on the basis of the total weight of the catalyst composition.

6. The method of claim 3, in which the total amount of (a) and (b) is 0.2–60% by weight on the basis of the total weight of the catalyst composition.

7. The method of claim 4, in which the total amount of (a) and (b) is 0.2–60% by weight on the basis of the total weight of the catalyst composition.

* * * * *